United States Patent
Meziere et al.

(10) Patent No.: US 7,591,945 B2
(45) Date of Patent: Sep. 22, 2009

(54) SUPPORT DEVICE FOR CONTAINERS IN EXTRACORPOREAL BLOOD TREATMENT MACHINES

(75) Inventors: Cyril Meziere, Bron (FR); Claudio Tonelli, Modena (IT); Vincenzo Baraldi, Quistello (IT); Massimo Zaccarelli, San Felice sul Panaro (IT); Jacques Chevallet, Serezin du Rhone (FR); Jean Louis Fressinet, Saint Jean de Touslas (FR); Yves Audouard, Moins (FR)

(73) Assignee: Gambro Lundia AB (SE)

( * ) Notice: Subject to any disclaimer, the term of this patent is extended or adjusted under 35 U.S.C. 154(b) by 657 days.

(21) Appl. No.: 10/771,289

(22) Filed: Feb. 5, 2004

(65) Prior Publication Data

US 2004/0154966 A1     Aug. 12, 2004

Related U.S. Application Data

(60) Provisional application No. 60/469,840, filed on May 13, 2003.

(30) Foreign Application Priority Data

Feb. 7, 2003   (IT) .......................... MI2003A0216

(51) Int. Cl.
*A61M 37/00* (2006.01)
*C02F 1/44* (2006.01)

(52) U.S. Cl. ...................... 210/85; 604/4.01; 604/5.01; 604/6.01; 210/645

(58) Field of Classification Search ................ 604/4.01, 604/5.01, 5.04, 6.09, 6.11, 6.16; 210/645–647, 210/321.6, 90, 195.2, 525, 232; 417/477.2, 417/237, 439; 422/44; 211/204, 205, 195
See application file for complete search history.

(56) References Cited

U.S. PATENT DOCUMENTS 4,044,983 A    8/1977   Francis ...................... 248/293
4,175,602 A    11/1979  Cavalaris et al. ............... 150/3

(Continued)

FOREIGN PATENT DOCUMENTS

DE    10023600    2/2002

(Continued)

OTHER PUBLICATIONS

International Search Report for International Application No. PCT/IB2004/000061.

(Continued)

*Primary Examiner*—Leslie R Deak
(74) *Attorney, Agent, or Firm*—Finnegan, Henderson, Farabow, Garrett & Dunner L.L.P.

(57) ABSTRACT

The support device for bags, applicable in machines for extracorporeal blood treatment or in machines for renal failure treatment, comprises a base body (2) and a support element (3) associated to the base body in such a way as to be displaceable with respect to the base body between at least one operative loading position and an operative work position. In particular the support element is telescopically engaged to the base body and is slidable along a predetermined movement direction (4). The special configuration of the support device enables an easy loading of the machine and a subsequent optimal control of the machine stability.

39 Claims, 5 Drawing Sheets

U.S. PATENT DOCUMENTS

| | | | |
|---|---|---|---|
| 4,961,557 A | 10/1990 | Garvin et al. | 248/318 |
| 5,445,613 A * | 8/1995 | Orth | 604/66 |
| 5,722,947 A | 3/1998 | Jeppsson et al. | 604/29 |
| 5,725,776 A | 3/1998 | Kenley et al. | 210/646 |
| 5,762,782 A | 6/1998 | Kenley et al. | 210/85 |
| 6,123,847 A * | 9/2000 | Bene | 210/646 |
| 6,350,249 B1 | 2/2002 | Zicherman | 604/29 |
| 6,355,161 B1 * | 3/2002 | Shah et al. | 210/91 |
| 6,390,311 B1 | 5/2002 | Belokin | 211/204 |
| 6,514,980 B1 | 2/2003 | Boyd | |
| 6,540,183 B1 | 4/2003 | Preuss | |
| 2002/0151804 A1 * | 10/2002 | O'Mahony et al. | 600/504 |

FOREIGN PATENT DOCUMENTS

| | | |
|---|---|---|
| EP | 0829 265 | 3/1996 |
| GB | 92 01 579.4 | 5/1992 |
| WO | WO 97/02056 | 1/1997 |

OTHER PUBLICATIONS

Concise Statement of Relevance of DE 10023600 (previously submitted on Aug. 13, 2004).

Concise Statement of Relevance of patent document DE G 9201579.4 (previously submitted on Aug. 13, 2004).

English Language Abstract of DE 10023600, Thomson Derwent.

English language Abstract of DE 9201579.

* cited by examiner

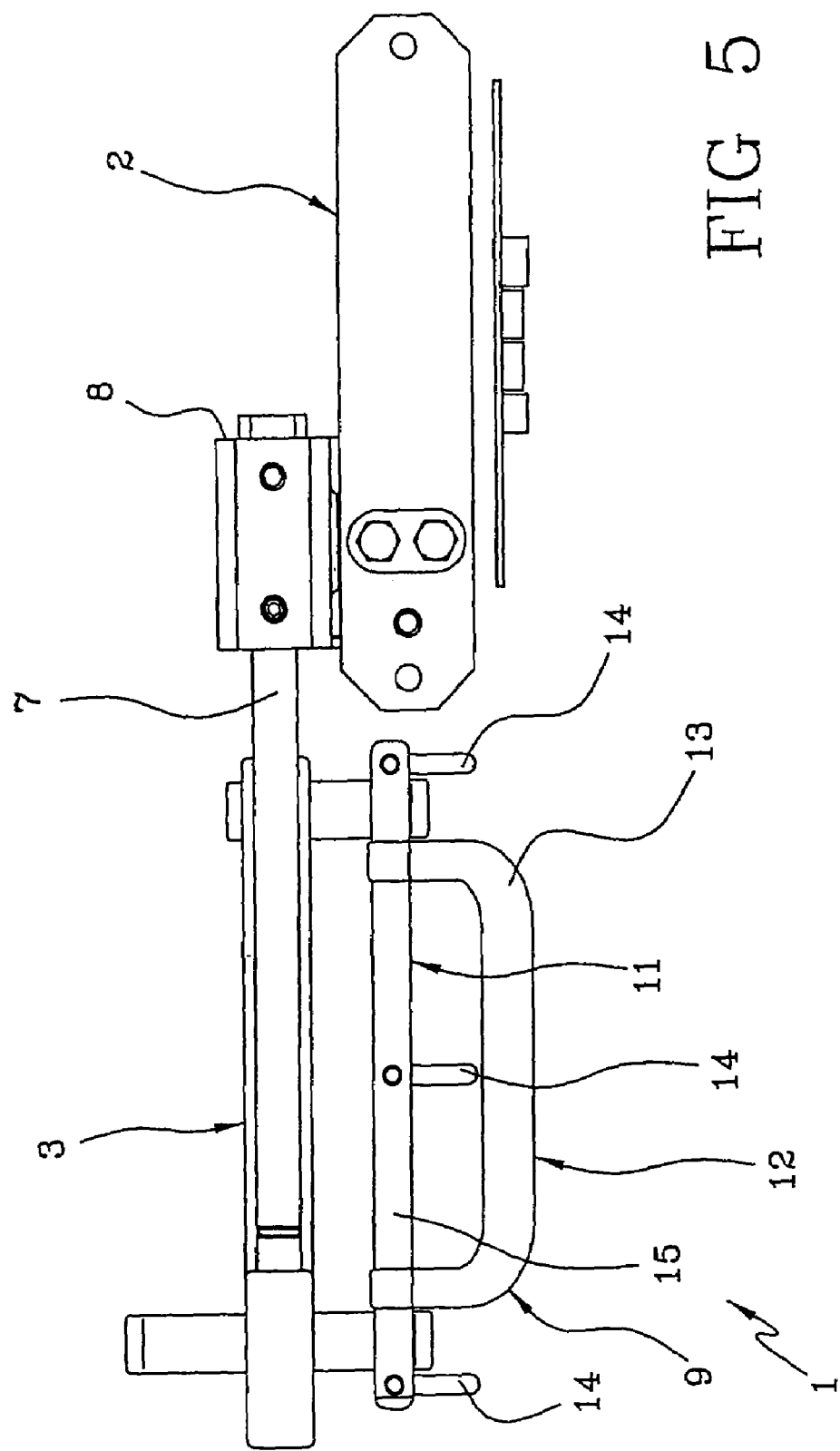

SUPPORT DEVICE FOR CONTAINERS IN EXTRACORPOREAL BLOOD TREATMENT MACHINES

CROSS REFERENCE TO RELATED APPLICATIONS

This application claims the priority of Italian Patent Application No. MI2003A000216, filed on Feb. 7, 2003, and the benefit of U.S. Provisional Application No. 60/469,840, filed May 13, 2003, the contents of which are incorporated herein by reference.

BACKGROUND OF THE INVENTION

The invention relates to a support device for containers, for extracorporeal blood treatment machines, or for renal failure treatment machines.

In more detail, the support device is destined to hold in position a predetermined number of bags containing the appropriate liquids destined for the various therapies which the patient will undergo.

As is known, the market already offers various machines for extracorporeal blood treatment, or for treatment of renal insufficiency, which machines are provided with respective support devices associated to the machine.

A first type of these support devices is constituted by arms, for example metal arms, which are engaged to the structure, directly constrained to the machine at an upper portion of the machine and provided at ends of the arms with one or more hooks which the bags containing the treatment liquids are attached to.

Another type of intensive therapy machine has these support devices located at a lower portion of the machine, so that the bags are attached in a position which is below the body of the machine.

Obviously, the second above type of machine has an improved stability with regard to the first, especially concerning jogs and sharp impacts in general to the machine in use, as the whole device's centre of gravity is kept as close as possible to the ground.

Though the prior art contains various bag support devices for machines destined for renal failure treatment or extracorporeal blood treatment, these devices have proved to be susceptible to improvement of various natures.

First of all, it is to be noted that the machines provided with support devices located above the machines themselves can lead not only to the above-mentioned problems connected with unexpected impacts and displacements, but also create problems related to the sometimes laborious and problematic operations of machine loading, i.e. the necessary lifting of a plurality of bags into the high position, and the need to make sure they are correctly engaged to the supports.

On the other hand, machines with the support devices located in the lower portion of the machine body require, for reasons of stability, that the bags be positioned as close as possible to the vertical axis of the machine in order not to laterally displace the machine centre of gravity.

The above requirement leads to the need to position the containers below the machine body, in a zone which is difficult to access both visually and manually.

SUMMARY OF THE INVENTION

In this situation, the main aim of the present invention is to resolve the above-described drawback in the prior art.

A first aim of the invention is to maintain optimum stability of the machine in the face of impacts and displacements, both when the machine is not loaded with bags containing liquids and after the bags have been loaded.

A further aim of the invention is to provide a support device which enables easy bag-positioning operations, therefore ensuring, when the machine is being loaded, a simpler visual and manual access thereto.

Finally, a further aim of the invention is to limit the machine weight and dimensions as much as possible.

These and other aims will better emerge in the description that follows, of a support device for bags, for extracorporeal blood treatment machines or for renal failure treatment machines, according to what is set out in the appended claims.

BRIEF DESCRIPTION OF THE DRAWINGS

Further characteristics and advantages of the invention will better emerge from the following detailed description of a specific embodiment, here described by way of non-limiting example with reference to the figures of the drawings, in which:

FIGS. 4 and 5 are views from above of the device of FIGS. 1 and 2;

DETAILED DESCRIPTION

Figure 1:
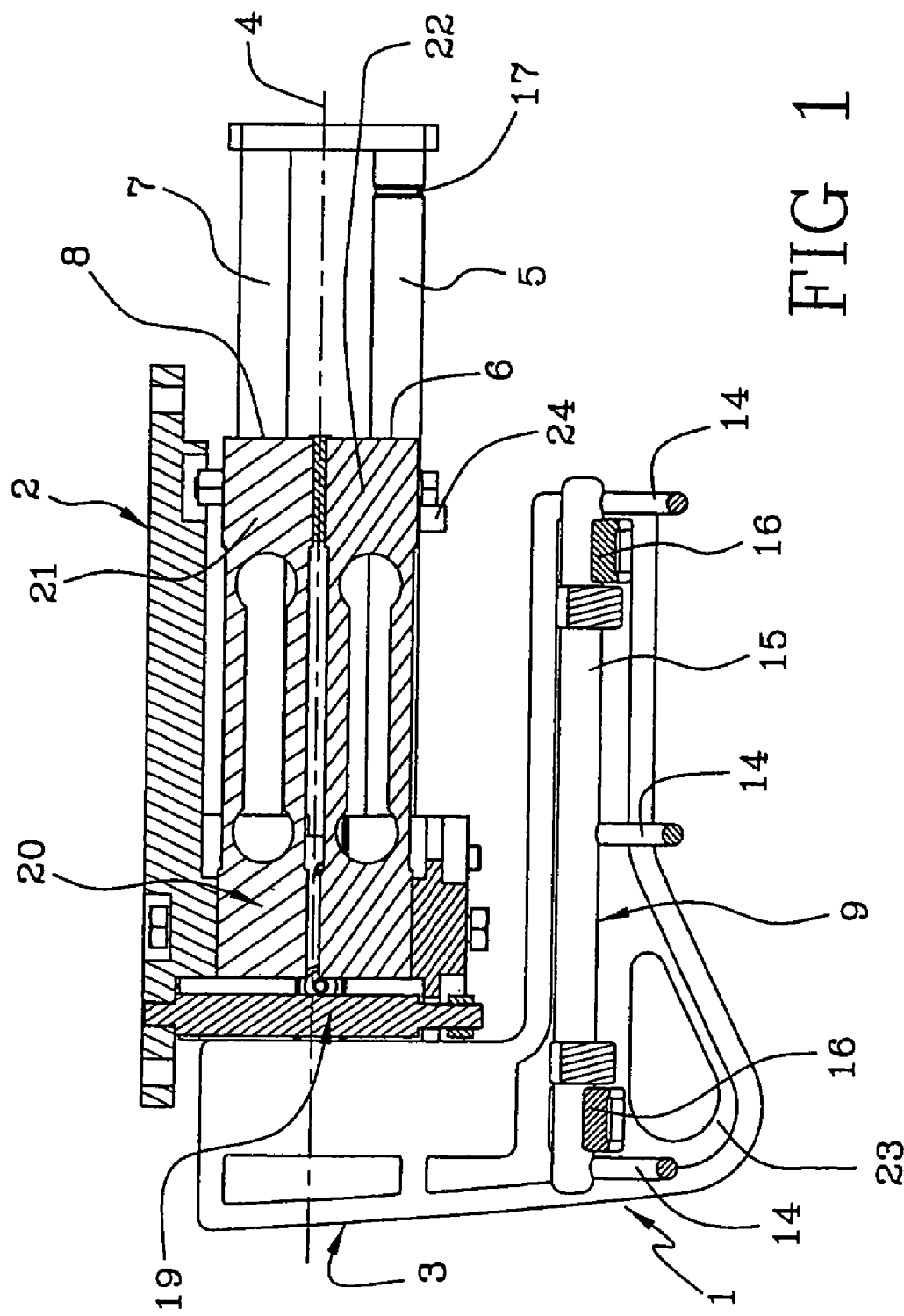
FIG. 1 is a side view of a support device according to the invention, in a minimum extension configuration.

With reference to the figures of the drawings, 1 denotes in its entirety a support device for containers or bags for machines for extracorporeal blood treatment or for renal insufficiency treatment.

As can be observed in FIGS. 1 to 5, the bag support device 1 comprises a base body 2, which base body 2 is generally (though not necessarily) constrained rigidly to a lower zone of a machine 100.

Obviously the device can be mounted in other parts of the machine, even above the machine body.

Generally speaking, however, the base body 2 is located below the body of the machine to enable a subsequent housing of the various bags 10 destined for use in the blood treatment operations or renal failure treatment operations in a free space afforded below the machine to which the support device is associated (see in particular FIG. 7, in which however the base body 2 is not visible).

In other words the machine affords a housing space 28 between the machine body 27, an upright structure 26 extending away from a floor base 25 and the same base 25.

The support device will be housed in the housing space 28 engaged to the machine body 27 and the upright structure 26.

This particular configuration means that the axis of the centre of gravity of the whole machine is maintained within the structure of the rest base when the machine is loaded with bags or when it is free of bags, whether the device is closed in the retracted position or open in the extracted position.

Figure 4:
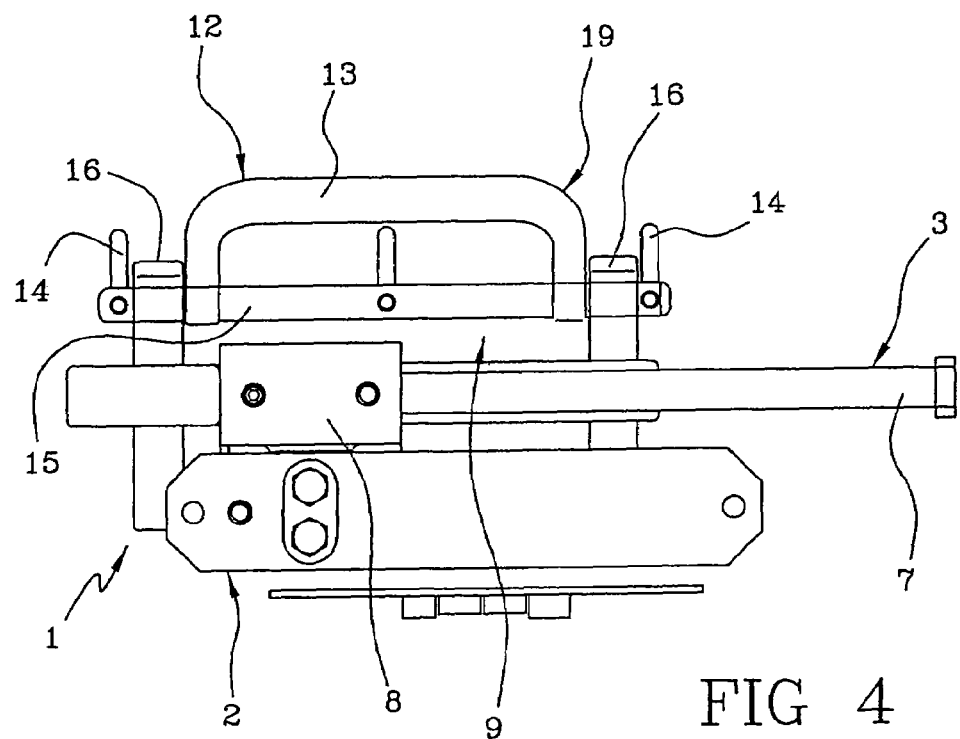
Figure 7:
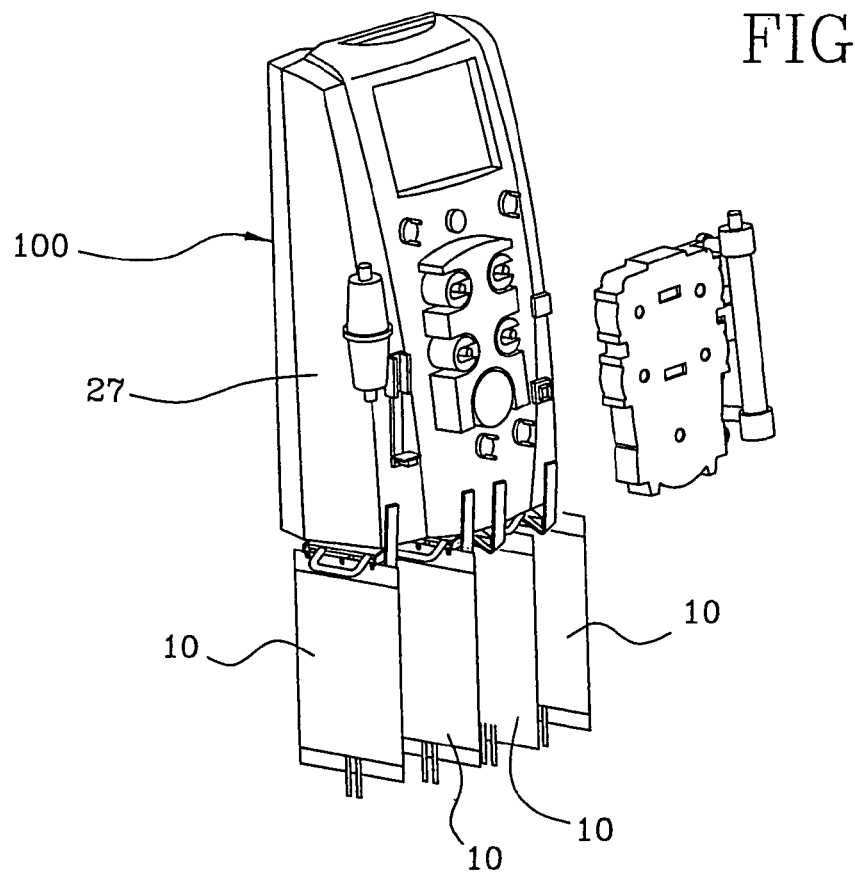
FIG. 7 is the machine of FIG. 6 loaded with a plurality of containers.
Figure 6:
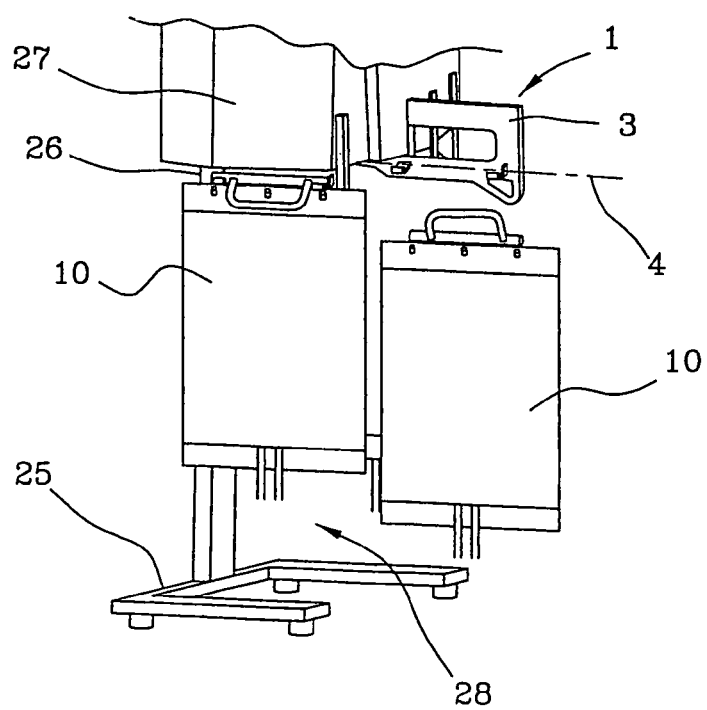
FIG. 6 is a schematic and perspective view of a machine for intensive therapy provided with the support device of FIG. 1.

As well as the base body 2, the device also comprises a support element 3 associated to the base body 2, which support element 3 can be moved with respect to the base body 2 between at least an operative loading position (FIGS. 2, 5 and 6) and an operative work position (FIGS. 1, 4 and 7).

In other words, the support element 3 is slidingly mobile between the operative loading position, corresponding to an essentially maximum extraction position of the support element 3 from the base body 2, and the operative work position, corresponding to an essentially minimum extraction position of the support element 3 in relation to the base body 2.

In the illustrated embodiment, the support element 3 moves between the above-cited positions along a movement direction 4 lying in an essentially horizontal plane.

The support device for containers passes from one to the other position by translating movements.

A possible further embodiment could be inserting a hinge between the base body 2 and the support element 3 so that the displacement between the operative loading position and the operative work position could follow a rotary displacement or a combination of rotary and translating movements.

From a structural point of view the support element 3 exhibits at least one and, in the illustrated embodiment, two elongate arms 5, 7 which are slidable in respective guides 6, 8 of the base body 2, defining a telescopic structure.

Also, should a longer extraction run be necessary, it would be possible to include a telescopic structure having more than one telescopic guide, for example, one telescoping guide into another.

The support element 3 is provided with suitable means 9 for supporting a container 10.

The means 9 for supporting can be constituted by at least one body 11 which is removably constrainable to the support element 3.

The body 11 will be equipped with at least one support hook 14, and usually with at least two and specifically three support hooks 14, destined to receive respective containers 10.

The body 11 will also be provided with an organ for manual transport 12, for example a handle 13.

Figure 2:
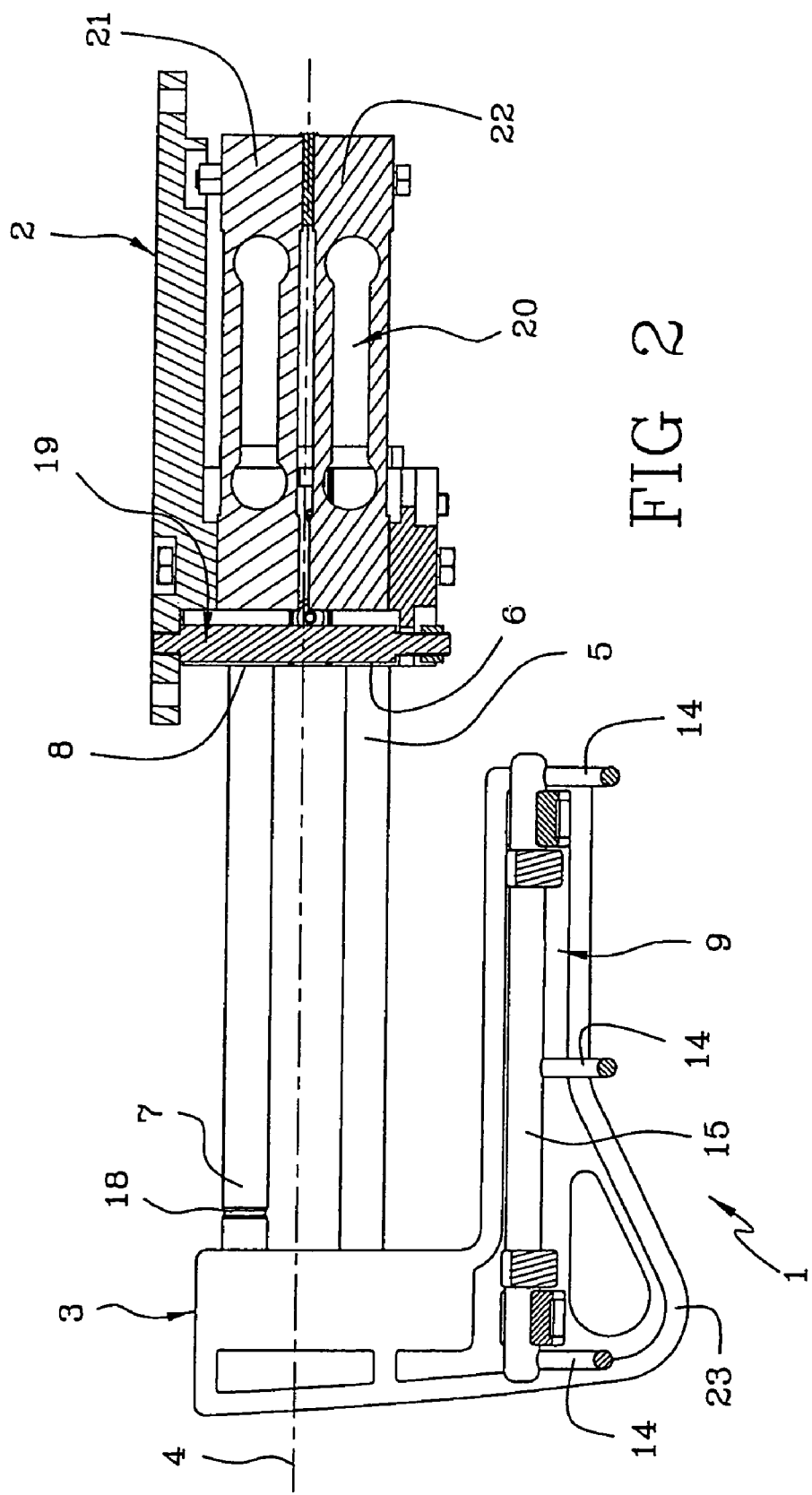
FIG. 2 is the device of FIG. 1, in a maximum extraction configuration.
Figure 3:
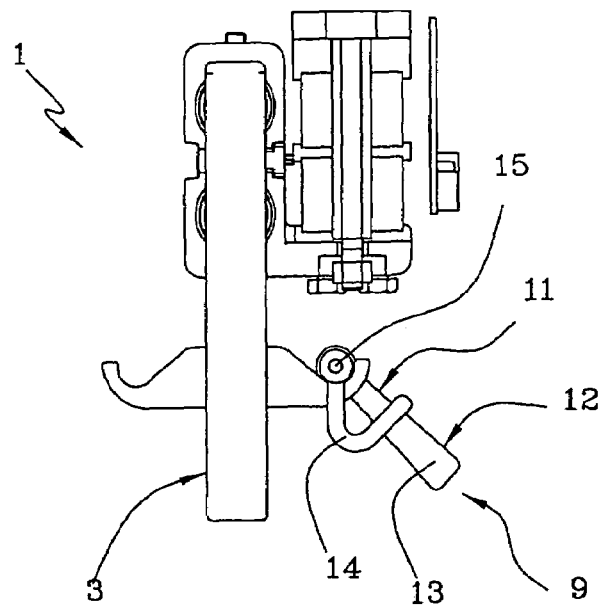
FIG. 3 is a side view of the device of FIG. 1.

As the body 11 is removably constrainable to the support element 3, it can be separated there-from, a bag can be engaged on the respective hooks 14 and by means of the handle 13 the bag can be easily constrained to the support device by resting a rod 15 of the body 11 on special supports 16 exhibited by the support element and clearly visible in FIGS. 2 and 3.

The support element 3 is further equipped with a manoeuvring handle 23 for enabling manual displacement between the operative work position and the operative loading position, and vice versa.

Obviously, instead of or together with the manoeuvring handle 23, an automatic movement system could be installed, in which the support element 3 could be commanded to displace between the various operative positions.

As can be observed in the figures, the support element 3 is provided with at least one mechanical endrun stop 17 for the operative loading position.

The endrun stop 17 can be a groove, for example located on the elongate arm 5 (see especially FIG. 1).

The support element 3 will also have at least one further endrun stop 18 for the operative work position.

In this case too, the mechanical endrun stop 18 can be a groove, for example, located on the elongate arm 7 (see especially FIG. 2).

The support device for bags further comprises at least one position sensor 19 associated to the base body 2 and able to recognise at least the arrival of the support element 3 in the operative work position.

The sensor will, usually, be a Hall sensor of known type and not further described herein.

Obviously, with the position sensor 19 it will be possible, should the need arise, to detect any position of the support element 3 relative to the base body 2.

The base body 2 is provided with weight sensors 20 for calculating the weight of a container 10 associated to the support device.

In particular, the sensors 20, for determining the weight, comprise at least one balance 21, which will send a signal proportional to the detected weight of the bag to a control unit. A further, controlling, balance 22 could be included to supply a further signal proportional to the weight of the bag, in effect controlling the reading of the other balance 21.

The device further comprises stop means 24 for selectively blocking the relative position of the support element 3 with respect to the base body 2 at least in the operative loading position and/or in the operative work position.

The stop means 24 can be constituted by a simple manually-activated or automatic pawl which cooperates with the elongate arms 5, 7 to block the arms in the desired relative positions.

Alternatively an actuator organ coordinated by a CPU can be included, to block at least one of the elongate arms 5, 7 on reaching a desired position.

The stop means 24 are normally active in blocking the support element in a retracted position, so as to prevent an undesired extraction of the arms 5, 7 when the machine is moved.

The stop means 24 are controlled, for example by an analog or digital control device, to enable contemporary extraction of a predetermined number of arms and bags. For example, if the predetermined number is one, the stop means 24 enable extraction of a single support at a time, automatically blocking the other supports in the retracted position. When the extracted support is returned to the retracted position the stop means 24 enable another or the same support to be extracted once more.

When the machine is unloaded, and loading of containers is about to begin, the support element is extracted, moving from the minimum extraction position from the base body 2 into the operative loading position (i.e. the maximum extraction position).

At this point the means 9 for supporting a container are brought into use, which are removed from the support element so that a bag can be engaged on the relative hooks.

Using the handle 13 the bag is positioned on the support element in a correct position and then the support element 3 is brought back into the operative work position.

The device may be designed so that the loading of a container 10 can be carried out exclusively in the operative loading position of the support element 3, in order to avoid the possibility of incorrect assembly operations.

The signal coming from the balance 21 will be sent and read as correct only when the container and the support element 3 are in the operative work position.

The invention offers important advantages.

Firstly, the use of a support device having a telescopic structure affords a very easy and functional loading operation of the bags for dialysis treatment and/or blood treatment on the patient.

In particular, as the support element 3 can be extracted, visual and manual access becomes extremely easy, and being in the lower position access for the operator is extremely comfortable.

Once the support arm is brought into the operative work position the added weight due to the presence of the bags is located as closely as possible to the ground and to machine centre of gravity.

Thus stability in the face of jogs, impacts and sharp movements is optimised; and the space taken up by the whole machine is diminished.

All of the various activities of the machine, controlled by a control unit, are started up only when the bag is correctly positioned below the machine, preventing erroneous activation on the part of the operator or activation of the machine when working conditions are not optimal.

The invention claimed is:

1. A support device for containers of liquids in extracorporeal blood treatment machines, or in renal failure treatment machines, comprising:

a base body;

a support element associated to the base body, the support element being displaceable with respect to the base body between at least one operative loading position, corresponding or close to a position of maximum extraction of the support element from the base body, and an operative work condition, corresponding or close to a position of minimum extraction of the support element from the base body, the support element comprising means for hanging a container;

sensors for weighing a container fixed to the base body, said sensors for weighing comprising at least one measuring balance for weighing a container hung to the support device, the means for hanging the container and the container being configured below the measuring balance in the work condition of the support element, the means for hanging the container and the container being configured laterally of the measuring balance in the loading position of the support element, and a control unit configured to receive, from the measuring balance, a signal proportional to the weight of the container, the control unit being further configured to read and validate the signal proportional to the weight of the container only in the operative work condition of the support element in which the means for hanging the container and the container are placed below the measuring balance.

2. The device of claim 1, wherein the support element is slidable between the operative loading position and the operative work position along a movement direction.

3. The device of claim 2, wherein the movement direction lies in an essentially horizontal plane when the support device is operating.

4. The device of claim 2, wherein the support element comprises at least one elongate arm that is slidable in a guide of the base body in order to displace between the operative loading position and the operative work position.

5. The device of claim 4, wherein the support element comprises two elongate arms that are slidable in guides of the base body in order to displace between the operative loading position and the operative work position.

6. The device of claim 1, wherein the support element is movable between the operative loading position and the operative work position by means of at least a translating or rotary displacement.

7. The device of claim 1, wherein the means for supporting comprise at least one body that is removably constrainable to the support element for supporting said container.

8. The device of claim 7, wherein the base body is intended for directly supporting said container.

9. The device of claim 7, wherein the base body is constrainable to the support element, said base body exhibiting a manual transport organ and at least one support hook for said container.

10. The device of claim 9, wherein the manual transport organ is a handle.

11. The device of claim 9, wherein the base body comprises at least two support hooks for receiving said container.

12. The device of claim 9, wherein the base body constrainable to the support element comprises a rod that bears the manual transport organ and said at least one support hook, the support element exhibiting supports for receiving and engaging the rod.

13. The device of claim 1, wherein the support element is provided with at least one mechanical endrun stop for the operative loading position.

14. The device of claim 13, wherein the mechanical endrun stop is defined by a groove.

15. The device of claim 1, wherein the support element is provided with at least one further mechanical end run stop for the operative work position.

16. The device of claim 15, wherein the further mechanical endrun stop is defined by a groove.

17. The device of claim 1, further comprising at least one position sensor, associated to the base body, for detecting at least the operative work position of the support element.

18. The device of claim 17, wherein the position sensor is a Hall sensor.

19. The device of claim 1, wherein the sensors for weighing further comprise a control balance, said control balance being a further balance, the control unit receiving a signal proportional to the weight of the container to verify that the measuring balance is working correctly.

20. The device of claim 1, wherein the support element further comprises a manoeuvring handle for enabling a manual displacement between the operative work position and the operative loading position, and vice versa.

21. The device of claim 1, wherein a loading of a container is excluded in the operative work condition of the support element.

22. The device of claim 1, further comprising stop means blocking a relative position of the support element with respect to the base body in the operative loading position and in the operative work position.

23. The device of claim 22, wherein the stop means are normally active for blocking the support element in a retracted position thereof.

24. A support device for containers of liquids in extracorporeal blood treatment machines, or in renal failure treatment machines, comprising:

a base body;

a support element associated to the base body, the support element being guided and translating with respect to the base body in a horizontal plane between at least one operative loading position, corresponding or close to a position of maximum extraction of the support element from the base body, and an operative work condition, corresponding or close to a position of minimum extraction of the support element from the base body, the support element comprising means for hanging a container and further comprising at least one elongated arm horizontally slidable inside a corresponding horizontal guide of the base body in order to displace between the operative loading position and the operative work position; and a lower zone of a machine, the base body being fixed to said lower zone of the machine and being interposed in use between the lower zone and the means for hanging the container, the means for hanging the container being placed in use below the lower zone of the machine and the base body.

25. The device of claim 24, further comprising sensors for weighing a container associated to the support device.

26. The device of claim 25, wherein the sensors for weighing comprise at least one measuring balance.

27. The device of claim 26, wherein said measuring balance for weighing is associable to a machine control unit, which is provided with a CPU configured to receive a signal proportional to a weight provided by the balance for weighing; said CPU being configured to validate said signal relating to the weight only when the support element is in the operative work position.

28. The device of claim 24, wherein the elongated arm and the horizontal guide define a telescopic structure.

29. The device of claim 24, wherein the support element comprises a further arm supporting said means for hanging a container, said further arm being placed outside the guide of the base body and movable between a loading position in which the further arm is placed laterally of the base body and a work condition in which the further arm is placed below the base body.

30. The device of claim 29, wherein the support element comprises a connecting portion for joining the elongated arm and the further arm, the connecting portion being laterally placed with respect to the base body both in the loading position and in the work condition.

31. The device of claim 30, wherein the support element comprises two elongate arms horizontally slidable in guides of the base body in order to displace between the operative loading position and the operative work position.

32. The device of claim 31, wherein the connecting portion joins together both the elongated arms and the further arm supporting said means for hanging a container.

33. A supporting apparatus comprising:
- a plurality of support devices for containers of liquids in extracorporeal blood treatment machines, or in renal failure treatment machines, each presenting:
- a base body;
- a support element associated to the base body, the support element being displaceable with respect to the base body between at least one operative loading position, corresponding or close to a position of maximum extraction of the support element from the base body, and an operative work condition, corresponding or close to a position of minimum extraction of the support element from the base body;
- stop means for selectively blocking a relative position of each support element with respect to the base body, at least in the operative loading position or in the operative work position; and
- a control unit configured to control the stop means to enable contemporary extraction only of a predetermined number of support elements of the support devices.

34. The apparatus of claim 33, wherein the stop means are normally active for blocking the support element in correspondence of the operative work condition where the support element is in a retracted position.

35. The apparatus of claim 33, wherein the control unit is of the type selected in the group comprising: an analog control device or a digital control device.

36. The apparatus of claim 33, wherein the predetermined number is one, and wherein the control device controls the stop means to enable extraction of a single support at a time, automatically blocking the other support elements in the operative work condition where the support element is in the retracted position.

37. The apparatus of claim 36, wherein the control device controls the stop means to enable another or the same support to be extracted once more, when the extracted support is returned to the operative work condition.

38. A support device for containers of liquids in extracorporeal blood treatment machines, or in renal failure treatment machines, comprising:
- a base body; and
- a support element associated to the base body, the support element being displaceable with respect to the base body between at least one operative loading position, corresponding or close to a position of maximum extraction of the support element from the base body, and an operative work condition, corresponding or close to a position of minimum extraction of the support element from the base body, the support element comprising:
- means for hanging a container;
- container weighing sensors fixed to the base body, said sensors comprising at least one measuring balance, configured to weigh a container hung to the support device, and at least one control balance, said means for hanging the container and the container being placed below the measuring balance in the work condition of the support element, and said means for hanging the container and the container being placed laterally of the measuring balance in the loading position of the support element; and
- a control unit configured to receive, from the measuring balance, a signal proportional to the weight of the container, the control unit being further configured to read and validate the signal proportional to the weight of the container only in the operative work condition of the support element in which the means for hanging the container and the container are placed below the measuring balance, the control unit configured to receive a signal proportional to the weight of the container to verify the correct working of the measuring balance.

39. A support device for containers of liquids in extracorporeal blood treatment machines, or in renal failure treatment machines, comprising:
- a base body; and
- a support element associated to the base body, the support element being guided and translating with respect to the base body in a horizontal plane between at least one operative loading position, corresponding or close to a position of maximum extraction of the support element from the base body, and an operative work condition, corresponding or close to a position of minimum extraction of the support element from the base body, the support element comprising:
- means for hanging a container;
- a lower zone of a machine, the base body being fixed to said lower zone of the machine and being interposed in use between the lower zone and the means for hanging the container, the means for hanging the container being placed in use below the lower zone of the machine and the base body;
- additional container weighing sensors associated to the support device, wherein the container weighing sensors comprise at least one measuring balance, said measuring balance being associable to a machine control unit, said machine control unit being provided with a CPU configured to receive a signal proportional to a weight provided by the measuring balance, said CPU being configured to validate said signal relating to the weight only when the support element is in the operative work position.

* * * * *

UNITED STATES PATENT AND TRADEMARK OFFICE
CERTIFICATE OF CORRECTION

PATENT NO. : 7,591,945 B2  
APPLICATION NO. : 10/771289  
DATED : September 22, 2009  
INVENTOR(S) : Cyril Meziere et al.

It is certified that error appears in the above-identified patent and that said Letters Patent is hereby corrected as shown below:

\*In claim 15, column 6, line 4, "end run" should read --endrun--.

Signed and Sealed this

Tenth Day of November, 2009

David J. Kappos  
*Director of the United States Patent and Trademark Office*